United States Patent [19]
Bible et al.

[11] Patent Number: 5,819,768
[45] Date of Patent: Oct. 13, 1998

[54] WAX FILLED DENTAL FLOSS

[75] Inventors: Kenan Oris Bible, Del Rio; Edward Sherman; Lloyd Etter, both of Morristown, all of Tenn.

[73] Assignee: Anchor Advanced Products, Inc., Knoxville, Tenn.

[21] Appl. No.: 850,124

[22] Filed: May 1, 1997

Related U.S. Application Data

[63] Continuation of Ser. No. 532,228, Sep. 21, 1995, abandoned.

[51] Int. Cl.$^6$ ...................................................... A45D 4/18
[52] U.S. Cl. ............................ 132/321; 132/323; 132/325
[58] Field of Search ..................... 132/321, 323, 132/329, 324, 325, 326, 327, 328; 424/443, 400

[56] References Cited

U.S. PATENT DOCUMENTS

| | | | |
|---|---|---|---|
| 4,414,990 | 11/1983 | Yost | 132/321 |
| 4,776,358 | 10/1988 | Lorch | 132/321 |
| 5,033,488 | 7/1991 | Curtis et al. | 132/321 |
| 5,209,251 | 5/1993 | Curtis et al. | 132/321 |
| 5,220,932 | 6/1993 | Blass | 132/321 |
| 5,413,127 | 5/1995 | Hill | 132/321 |
| 5,503,842 | 4/1996 | Fazan et al. | 424/443 |

*Primary Examiner*—Gene Mancene
*Assistant Examiner*—Pedro Philogene
*Attorney, Agent, or Firm*—Godfrey & Kahn, S.C.

[57] ABSTRACT

A PTFE dental floss, filled with wax, and having no wax coating, which provides reduced likelihood of fraying and superior lubricity.

29 Claims, 1 Drawing Sheet

WAX FILLED DENTAL FLOSS

This is a continuation of Ser. No. 08/532,228, filed Sep. 21, 1995, now abandoned.

FIELD OF THE INVENTION

The present invention relates generally to dental cleaning floss and more particularly to a wax filled dental floss which does away with the need for a wax coating.

BACKGROUND OF THE INVENTION

It should be understood that the use of the term "dental floss" hereinafter is intended to encompass dental filaments, tapes and any similar article.

The removal of plaque and entrapped food particles reduces: cavities; the tendency towards gingivitis; and mouth odor. It also generally improves oral hygiene. Conventional brushing of teeth is not particularly effective in removing entrapped food particles from crevices between the teeth and/or removing plaque which enables bacteria to adhere to teeth.

The interproximal regions are of concern to the dental profession where continual prophylaxis should be maintained to ensure the greatest resistance to deteriorating conditions. Particles of food (carbohydrates, meat fibers, etc.) are trapped in these regions and often become incapable of removal by natural reflexes. Subsequent disintegration of these food particles, if not physically removed, provide a media for detrimental microorganisms which give off acids or enzymes which cause acid formation, and therefore account for deteriorating conditions in these interproximal regions.

Dental floss is commonly used to clean and remove food, plaque and tarter build-up from around and between teeth. Various forms of dental floss have been proposed and/or employed for cleaning the interproximal areas and other areas not accessible by a toothbrush. Conventional dental floss comprises a filament of a deformable or non-deformable material that is inserted between teeth thereby allowing cleaning of the teeth as the floss is moved along the tooth surface. The most common type of floss on the market is in the form of a small diameter, smooth surfaced twisted multi-filament strand that is pulled up and down and lengthwise, between teeth and against tooth surfaces.

Recently, a new type of "premium" dental floss made from polytetrafluoroethylene ("PTFE") has become available from a variety of sources. This type of dental floss has certain beneficial characteristics including extremely high lubricity and a lower fraying rate than conventional flosses. Three patents have been directed to such products including U.S. Pat. Nos. 5,033,488 and 5,209,251 to Curtis et al. (the "Curtis patents") and U.S. Pat. No. 5,220,932 to Blass (the "Blass patent").

The Curtis patents disclose the use of high strength (i.e., expanded) PTFE which is coated with a material to increase the PTFE's coefficient of friction for use as a dental floss.

The Blass patent discloses the use of a uniaxially stretched, non-porous PTFE having a relatively low tensile strength which is coated with wax to increase the PTFE's coefficient of friction for use as a dental floss.

Since untreated PTFE floss' desirable characteristics are offset by its extreme lubricity, i.e., it is virtually impossible for a user to hold during teeth cleaning, it must be treated to increase its coefficient of friction. To date, this increase has been achieved, as described in the Curtis and Blass patents, by coating the PTFE with wax. This coating has several drawbacks. First, the coating can be stripped, in whole or in part, from the PTFE during use, leaving a user with unwanted wax on his hands, teeth or in his mouth. Second, The necessity to coat the PTFE causes increased processing time and corresponding increased cost. Finally, the wax coating excessively stiffens the otherwise relatively supple PTFE.

SUMMARY OF THE INVENTION

It is therefore an object of the present invention to provide an improved dental floss which has substantially increased lubricity and reduced fraying without the need for the application of a wax or other coating.

This and other objects and advantages of the present invention will become apparent from the detailed description and accompanying drawings.

The dental cleaning floss of the present invention comprises one or more strands of PTFE, "filled" with wax. The invention differs from the prior art in that no wax or other coating is needed to increase the coefficient of friction of the PTFE floss. Rather, the inclusion of wax in the formation of the PTFE as a filler material acts to bring the coefficient of friction up to levels desirable for use as a dental floss.

Flavorings and other additives such as fluoride can be added to the wax filler. However, they can also be sprayed, in liquid form, onto the otherwise finished floss.

The present invention provides substantial advantages over the prior art in that it does not require the use of a wax or other coating to increase the coefficient of friction of PTFE to a suitable level for use as a dental floss. This yields at least three advantages including: the absence of a removable coating which could build up on teeth; retained suppleness of the PTFE material vis-a-vis wax coated PTFE; and lower time and cost production of a finished floss product.

In sum, the present invention represents a significant improvement over the prior art.

DETAILED DESCRIPTION OF THE INVENTION

Figure 1:
FIG. 1 is a microphotograph of a cross-sectional view of wax filled dental floss according to an embodiment of the present invention.

The present invention comprises at least one strand of PTFE, which may be uniaxially or biaxially stretched, which is filled with at least one material which is capable of increasing the coefficient of friction of PTFE, such as wax. The wax or other material is incorporated into the PTFE raw materials and extruded with the PTFE to form a "filled" PTFE.

Preferably, the dental floss of the present invention comprises a single strand of the filled PTFE made into the form of a tape having a thickness between about 0.001 to about 0.002 inches and a width between about 0.030 to 0.100 inches. The tensile strength of the filled PTFE floss is preferably between about 5 to about 25 pounds with a density of about 1.7 g/cm$^3$ to about 2.2 g/cm$^3$. The coefficient of friction of the floss is between about 0.08 to about 0.25. The denier value ranges from about 500 to about 1500 denier.

In another embodiment of the present invention, the dental floss comprises a plurality of threads of which at least one is made from the filled PTFE. The floss can be in the form of traditional twisted strand floss with other strands made from nylon, Dacron®, polyester, etc. or in the form of a braided floss as described in applicant's copending U.S. application Ser. No. 08/532,004 now U.S. Pat. No. 5,692, 530, entitled Braided Dental Floss, which application is incorporated herein by reference.

If the filled PTFE is used in a multi-strand, twisted floss, the preferred dimensions are about 0.0002 to about 0.003 inches for each PTFE strand and about 0.010 to about 0.025 inches for the overall floss.

As a filling material for the PTFE, a wide variety of waxes may be employed. The wax chosen should be suitable and safe for all use. The preferred wax is a microcrystalline wax which can be a natural wax (i.e. from insects, animals or plants), petroleum wax or a synthetic wax. In one embodiment of the present invention the wax is a beeswax. Beeswax has certain advantages when used as an ingredient with dental floss. It is a natural product with no known adverse indications for human use and therefore is more acceptable, particularly for an article which is to be used in the mouth. In addition, beeswax provides beneficial friction characteristics. Furthermore, beeswax is readily available. The amount of wax employed is preferably in the range of about 1 to about 15% weight percent of the total weight of the PTFE raw materials.

Flavor agents may also be used. The use of a flavored dental floss as opposed to an unflavored floss provides aesthetic advantages. This can make the floss more pleasant to use, to thereby encourage better oral hygiene practices. Preferably, flavor particles are spray dried onto the floss or mixed in with the PTFE raw materials and the wax. The particles consist essentially of a flavor oil dispersed in a matrix of a water soluble medium. The coating or additive preferably comprises about 1 to 10% by weight of the dental floss. The spray-dried flavor particles may comprise about 0.1% to about 8% by weight of the dental floss.

In another embodiment, the strands or threads are impregnated with a polymeric coating containing spray-dried flavor particles consisting essentially of a flavor oil dispersed in a matrix of a water-soluble medium with the water-soluble medium being capable of being dissolved by the saliva in the oral cavity when the floss is applied to the teeth thereby releasing the flavor to the teeth and oral cavity.

In yet another embodiment, the strands or threads are impregnated with a polymeric coating containing spray-dried flavor particles, wherein the polymeric coating is:

a. alkyl monoesters of poly(methyl vinyl ether/maleic acid) of the formula:

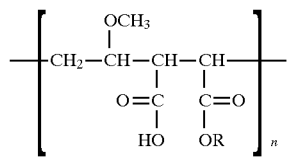

wherein R is an alkyl group containing from 1 to 4 carbon atoms or hydrogen and wherein n is from about 3,000 to 3,400;

b. polyvinyl pyrrolidones of the formula:

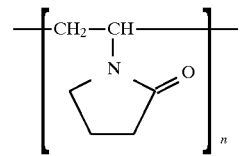

wherein n is from about 100 to 360;

c. acrylamide/acrylate/butylaminoethyl methacrylate polymers;

d. vinyl acetate/crotonic acid/vinyl neodecanoate terpolymers;

e. vinyl acetate/crotonic acid copolymers; and f. terpolyamides comprised of the copolymerization products of dicarboxylic acid-diamine reaction product, a second but dissimilar dicarboxylic acid-diamine reaction product and a lactim wherein said terpolyamides have a molecular weight of from about 12,000 to about 24,000.

In another embodiment, the polymeric coating is an alkyl monoester of poly(-methyl vinyl ether/maleic acid) of the formula:

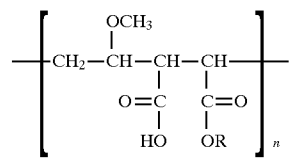

wherein R is selected from alkyl groups containing 1 to 4 carbon atoms and hydrogen and n is from 3000 to 3400.

In yet another embodiment, the polymeric coating is a polyvinyl pyrrolidone of the formula:

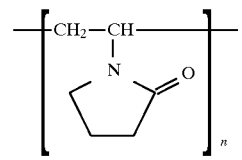

wherein n is from about 100 to 360.

The polymeric coating may also comprise an acrylamide/acrylate/-butylaminoethyl methacrylate polymer, a vinyl acetate/crotonic acid/-vinyl neodecanoate terpolymer, or a vinyl acetate/crotonic acid copolymer.

Alternatively, the polymeric coating may comprise a terpolyamide comprising the copolymerization product of a dicarboxylic acid-diamine reaction product, a second but dissimilar dicarboxylic acid-diamine reaction product and a lactim wherein said terpolyamides have a molecular weight of from about 12,000 to about 24,000.

In still another embodiment, the polymeric coating is:

a. alkyl monoesters of poly(methyl vinyl ether/maleic acid) of the formula:

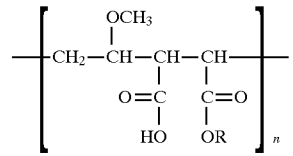

wherein R is an alkyl group containing from 1 to 4 carbon atoms or hydrogen and wherein n is from about 3,000 to 3,400;

b. polyvinyl pyrrolidones of the formula:

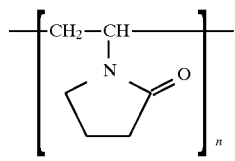

wherein n is from about 100 to 360;

c. acrylamide/acrylate/butylaminoethyl methacrylate polymers;

d. vinyl acetate/crotonic acid/vinyl neodacanoate terpolymers;

e. vinyl acetate/crotonic acid copolymers; and f. terpolyamides comprised of the copolymerization products of dicarboxylic acid-diamine reaction product, a second but dissimilar dicarboxylic acid-diamine reaction product and a lactim wherein said terpolyamides have a molecular weight of from about 12,000 to about 24,000.

The method of making the filled PTFE dental floss of the present invention comprises the steps of: making a slurry type mixture of standard PTFE precursor materials, the wax (and/or other coefficient of friction increasing material(s)) and other desired flavorings or additives; extruding the slurry material through a high pressure ram extruder at very high temperature (i.e., between about 300° F. to about 600° F.); drawing and stretching the extruded material uniaxially or biaxially until individual strands have a density of between about 1.7 g/cm$^3$ and 2.2 g/cm$^3$; and winding the strands of material on a pirn. If the dental floss is a multi-strand product, it is thereafter twisted with other strands of the same or different material in accordance with conventional floss twisting procedures. External flavorings or other additives can be added by coating or spraying after the floss is otherwise complete.

As illustrated by the foregoing description, the present invention has superior application as a dental floss for cleaning teeth. The filled PTFE dental floss of the present invention has superior lubricity and greater resistance to fraying, while avoiding the need for expensive and time consuming wax coating.

The terms and expressions which have been employed are used as terms of description and not of limitation, and there is no intention in the use of such terms or expressions of excluding any equivalence of the features shown and described as portions thereof, it being recognized that various modifications are possible without departing from the spirit or the intent of the invention.

We claim:

1. A dental floss comprising at least one modified strand of PTFE, said strand being free of any friction coating and having a coefficient of friction between about 0.08 and 0.25.

2. The dental floss of claim 1, wherein said at least one strand is in the form of a tape having a thickness of between 0.001 inches and 0.002 inches.

3. The dental floss of claim 2, wherein said at least one strand has a width between about 0.030 inches to about 0.100 inches.

4. The dental floss of claim 1, wherein said floss has a tensile strength of between about 5 to about 25 pounds.

5. The dental floss of claim 1, wherein each said at least one strand has a density between about 1.7 g/cm$^3$ and about 2.2 g/cm$^3$.

6. The dental floss of claim 1, wherein a plurality of said strands are braided together to form a floss.

7. The dental floss of claim 1, wherein a plurality of said strands are formed into threads which are braided together to form a floss.

8. The dental floss of claim 7, wherein each said strand is between about 25 and about 50 denier.

9. A dental floss comprising at least one strand of PTFE, free of any friction coating, wherein the coefficient of friction of the floss is between about 0.08 and about 0.25, wherein said at least one strand of PTFE is filled with at least one material capable of increasing the coefficient of friction.

10. The dental floss of claim 9, wherein said material capable of increasing the coefficient of friction is wax.

11. The dental floss of claim 10, wherein said wax is a microcrystalline wax.

12. The dental floss of claim 9 wherein said at least one strand is in the form of a tape having a thickness of between about 0.001 inches and about 0.002 inches.

13. The dental floss of claim 12 wherein said at least one strand has a width between about 0.030 inches and about 0.100 inches.

14. The dental floss of claim 9 wherein said floss has a tensile strength of between about 5 to about 25 pounds.

15. The dental floss of claim 9 wherein each said at least one strand has a density between about 1.7 g/cm$^3$ and about 2.2 g/cm$^3$.

16. The dental floss of claim 9 wherein a plurality of said strands are braided together to form a floss.

17. The dental floss of claim 9 wherein a plurality of said strands are formed into threads which are braided together to form a floss.

18. The dental floss of claim 17 wherein each of said strands is between about 25 and about 50 denier.

19. A dental floss comprising at least one strand of PTFE filled with microcrystalline wax, wherein the coefficient of friction of the floss is between about 0.08 and about 0.25 and wherein each said at least one strand has a density between about 1.7 g/cm$^3$ and about 2.2 g/cm$^3$.

20. A dental floss comprising at least one strand of PTFE, said at least one strand of PTFE internally containing at least one material for increasing the coefficient of friction of said at least one strand and having an outer surface which is free of any friction coating, wherein the coefficient of friction of the floss is between about 0.08 and about 0.25.

21. A friction coating free dental floss comprising: at least one strand of material formed by extruding PTFE with a material capable of increasing the coefficient of friction of PTFE, wherein the coefficient of friction of the floss is between about 0.08 and about 0.25.

22. A method of making dental floss comprising the steps of: combining PTFE raw materials and at least one material capable of increasing the coefficient of friction to form a slurry; extruding the slurry at high temperature to obtain an extruded material; stretching the extruded material; and winding the extruded material.

23. A method according to claim 22, wherein said at least one material capable of increasing the coefficient of friction is a wax.

24. A method according to claim 23, wherein said wax is a microcrystalline wax.

25. A method according to claim 24, wherein said microcrystalline wax is beeswax.

26. A method according claim 22, wherein said extruded material is uniaxially stretched.

27. A method according to claim 22, wherein the amount of said at least one material capable of increasing the coefficient of friction is between about 1% and about 15% weight percent of said PTFE raw materials.

28. A method according to claim 22, wherein the coefficient of friction of said stretched, extruded material is between about 0.08 and about 0.25.

29. A method according to claim 22, wherein said stretched, extruded material is in the form of tape.

* * * * *